United States Patent [19]

Van de Veen

[11] Patent Number: 5,545,232
[45] Date of Patent: Aug. 13, 1996

[54] DEVICE FOR MUTUAL PIVOTING CONNECTION OF PARTS OF AN ORTHOPAEDIC APPARATUS

[75] Inventor: Paul G. Van de Veen, Enschede, Netherlands

[73] Assignee: Otto Bock Orthopadische Industrie Besitz-und Verwaltungs-Kommanditgesesllschaft, Duderstadt, Germany

[21] Appl. No.: 392,355

[22] Filed: Feb. 21, 1995

[30] Foreign Application Priority Data

Feb. 22, 1994 [NL] Netherlands ............................. 9400269

[51] Int. Cl.⁶ ........................................................ A61F 2/64
[52] U.S. Cl. ................................................ 623/39; 623/44
[58] Field of Search ................................ 623/39, 40, 41, 623/42, 43, 44, 45; 602/16, 26

[56] References Cited

U.S. PATENT DOCUMENTS

| | | | |
|---|---|---|---|
| Re. 33,621 | 6/1991 | Lamb et al. | 623/39 |
| 2,638,605 | 5/1953 | Johnson | 623/44 |
| 4,064,569 | 12/1977 | Campbell | 623/43 |
| 4,215,442 | 8/1980 | Blatchford et al. | 623/39 |
| 4,961,416 | 10/1990 | Moore et al. | 602/26 |
| 5,181,931 | 1/1993 | Van de Veen | 623/40 |
| 5,201,776 | 4/1993 | Freeman | 602/26 |
| 5,314,498 | 5/1994 | Grammas | 623/39 |

FOREIGN PATENT DOCUMENTS 2194443  3/1988  United Kingdom ..................... 623/39

Primary Examiner—David H. Willse
Assistant Examiner—Bruce E. Snow
Attorney, Agent, or Firm—Whitham, Curtis, Whitham & McGinn

[57] ABSTRACT

The invention relates to a device for mutual pivoting connection of parts of an orthopaedic apparatus, such as in particular a knee prosthesis for leg amputees, comprising a kinematic multiple linkage system with at least four rods, adjoining rods of which have a common pivot axis and the pivot axes extend substantially mutually parallel.

19 Claims, 6 Drawing Sheets

DEVICE FOR MUTUAL PIVOTING CONNECTION OF PARTS OF AN ORTHOPAEDIC APPARATUS

The invention relates to a device for mutual pivoting connection of parts of an orthopaedic apparatus, such as in particular a knee prosthesis for leg amputees, comprising a kinematic multiple linkage system with at least four rods, adjoining rods of which have a common pivot axis and the pivot axes-extend substantially mutually parallel.

The use of multiple linkage systems to replace or support the joint function in orthopaedic apparatus has been known for a long time and is frequently applied on account of the advantages which such a system has compared to the more conventional mechanisms with one fixed hinge point. These advantages include inter alia a better following or imitation of the natural movement of the limbs compared with a single-axis mechanism and an increased and better controllable stability of the mechanism when it is loaded, and are achieved by a suitable choice of the dimensions and the mutual position of the rods of the system. Particularly when a multiple linkage system is used to replace or support the knee function, this latter is of great importance. It is essential at the beginning of a stepping movement, when the mechanism is extended, the heel touches the ground and the mechanism is loaded by the weight of the user, that the mechanism does not begin to pivot immediately, because the user would then not have any support and would fall. This can only be prevented in a single-axis mechanism by applying a complex and not very reliable braking mechanism. In a multiple linkage system on the other hand, this property can be obtained by selecting the geometry such that in the extended situation of the mechanism the virtual centre of rotation around which the lower leg or the lower leg prosthesis pivots lies behind the line which joins the two load points (the heel and the hip-joint).

A suitable choice of the geometry of the multiple linkage system can moreover achieve that the virtual centre of rotation at the end of a stepping movement is so located that the prosthesis or orthesis can be carried more simply into a forward swinging movement compared with a single-axis mechanism. The great stability to be achieved at the start of the stepping movement, the swing-back movement that is simple to generate and the possibility of finding in simple manner a good compromise between these two properties make the multiple linkage system excellently suited to replace or support a joint function.

An important prerequisite of a kinematic multiple linkage system in such applications is that it displays an initial compressing bending as the human knee also does. This has the result inter alia that the small initial compressing bending is present which is displayed by the real joint when it is loaded. The damping influence of the joint when the leg is loaded prevents progress of a jerky nature which can be unpleasant and in the long run even painful for the user. The initial bending under load further prevents a limitation of the vertical movement of the centre of gravity of the body, whereby the energy required for walking remains limited. This knee bending is called "stance flexion".

The existing devices for mutual pivoting connection of parts of an orthopaedic apparatus, such as in particular a knee prosthesis for leg amputees, have the drawback that the stance flexion is limited to 3°–4°. This is too little to fully realize the stated advantages of the stance flexion. Another drawback is formed by the connection point of a prosthesis located far to the rear. Particularly in the case of a so-called knee-exarticulation (a severing of the leg in the knee joint, that is, the upper leg is fully retained from the knee joint), this results in the drawback of the prosthesis coming to lie unacceptably far to the rear.

The invention has for its object to provide a device of the type stated in the preamble with which a stance flexion can be realized which is so great that it is possible to walk naturally therewith and wherein the one movement (stance flexion) blocks the other movement (swing flexion). The invention has the further object of providing a device with which it is possible to place the connection point for an orthopaedic apparatus sufficiently far forward, also in the case of a knee exarticulation. Yet another object of the invention is to provide a device which is simple in construction and reliable in use.

The invention provides for this purpose a device of the type stated in the preamble characterized in that a rod is pivotally connected only to an upper output rod and to a lower output rod, and a rod placed in walking direction behind the rod is pivotally connected on one side to the upper output rod and is connected on another side to the lower output rod such that when the device is pivoted this rear rod performs a constrained movement relative to the lower output rod which comprises translation as well as rotation. This device provides a desired functionality, a relatively large stance flexion combined with impeding of a second degree of freedom of movement, which can be realized in simple manner.

A preferred embodiment of the device is characterized in that the rear rod is connected with interposing of at least one coupling rod to the lower output rod, wherein the coupling rod is pivotally connected to both the rear rod and the lower output rod. Another preferred embodiment is characterized in that the rear rod is connected with interposing of two coupling rods to the lower output rod, wherein both coupling rods are pivotally connected to both the rear rod and the lower output rod and the rods form a so-called Stephenson six-linkage system. In the simple device with two coupling rods the rear rod can perform a constrained rotating and translating movement without additional steps. In the device with one coupling rod an additional step is necessary to obtain the constrained rotating and translating movement.

Another preferred embodiment is characterized in that the rear rod is connected with interposing of at least one three-linkage system to the lower output rod, which three-linkage system consists of a rod which is pivotally connected to the rear rod and which is pivotally connected at two positions to two connecting rods which are both pivotally connected to the lower output rod. A still more specific preferred embodiment is characterized in that the rear rod is connected with interposing of two three-linkage systems to the lower rod. These are variants of the devices referred to in claims 2 and 3 wherein the coupling rods are replaced by the three-linkage systems.

Yet another preferred embodiment is characterized in that the rear rod is connected by means of at least one pin/slot connection to the lower output rod. A specific embodiment hereof is formed in that the rear rod is connected by means of two pin/slot connections to the lower output rod. In these devices a coupling rod as referred to for instance in claims 2 and 3 or a three linkage system as stated in claims 4 and 5 is replaced by a pin/slot connection. Also with these steps the rear rod can perform a constrained rotating and translating movement.

A preferred embodiment of the device is characterized in that at least one Of the rods takes a multiple form. These multiple embodied rods increase the sturdiness of the device.

The device preferably comprises at least one spring-mounted element which is connected to at least two of the rods. A preferred embodiment of this spring-mounted element comprises a damper. The spring can be used for instance for easy carrying forward of the lower leg at the end of the swing phase. The damper can for instance be used for dissipating energy in the swing stage.

The present invention will be further elucidated with reference to the non-limitative embodiments shown in the following figures. Herein:

Figure 1:
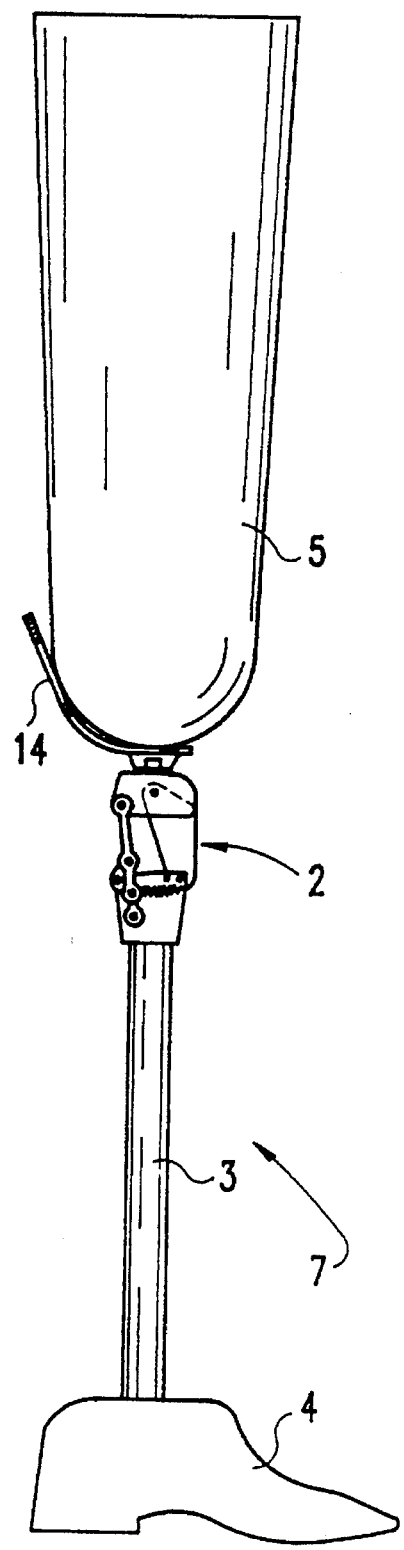
FIG. 1 shows a side view of a prosthesis for leg amputees.

FIG. 1 shows a prosthesis 1 for leg amputees in which a linkage system 2 fulfils the function of knee joint. Prosthesis 1 further comprises an artificial lower leg 3 with artificial foot 4 and means 5 for fixing prosthesis 1 to a leg stump.

Figure 2:
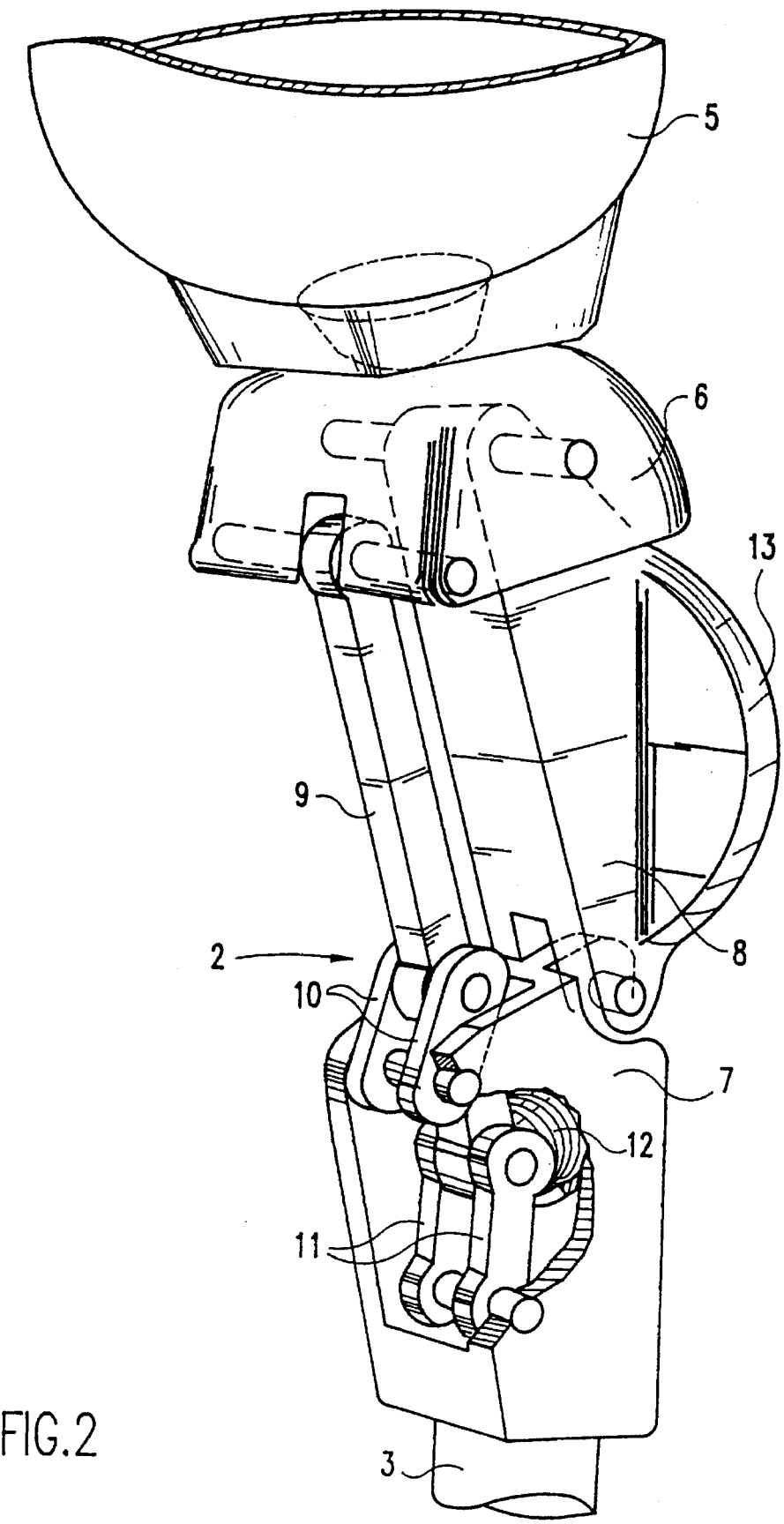
FIG. 2 is a perspective partly cut-away view of a part of the device shown in FIG. 1, FIG. 3–9 are schematic views of a six-linkage system according to the invention.

FIG. 2 shows the linkage system 2 in detail. The six-linkage system 2 shown in this figure is formed by an upper output rod 6—which is connected to the means 5 for fixing prosthesis ! to a leg stump—, a lower output rod 7—which is connected to the artificial lower leg 3 —, a rod 8 pivotally connected only to the said rods 6, 7, a rear rod 9 located in the walking direction behind rod 8—which rod 9 is pivotally connected to the upper output rod 6—, and two coupling rods 10, 11 which are both pivotally connected to the rear rod 9 and the lower output rod 7. The coupling rods 10, 11 take a double form for a greater sturdiness of the linkage system 2. The figure also shows spring means 12 for carrying forward the artificial lower leg 3 more easily. Rod 8 is provided with a kneecap-shaped front part 13 to give the exterior thereof the appearance of a human knee. The operation of this linkage system 2 will be further elucidated with reference to the following figures.

Figure 5:
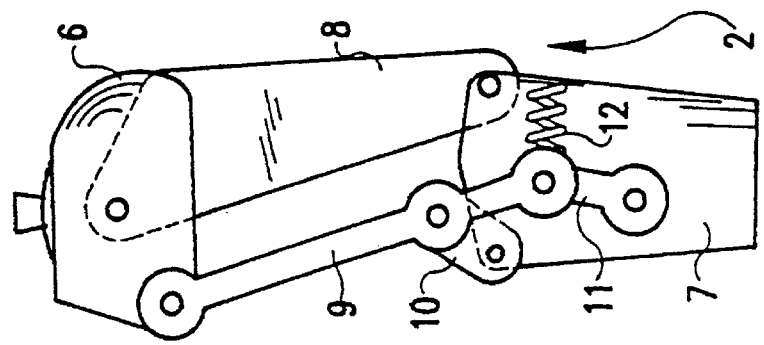
Figure 4:
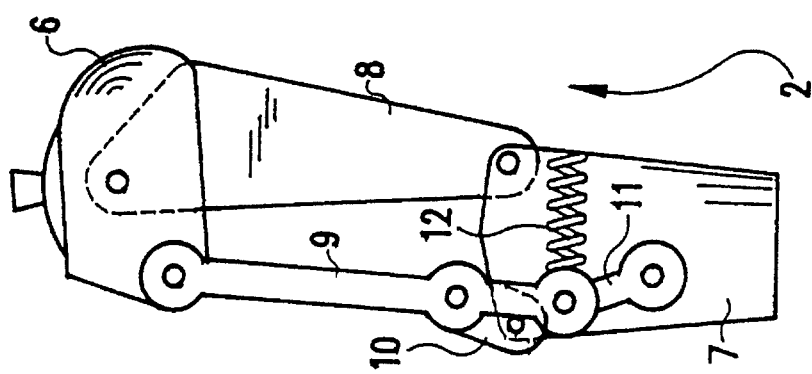
Figure 3:
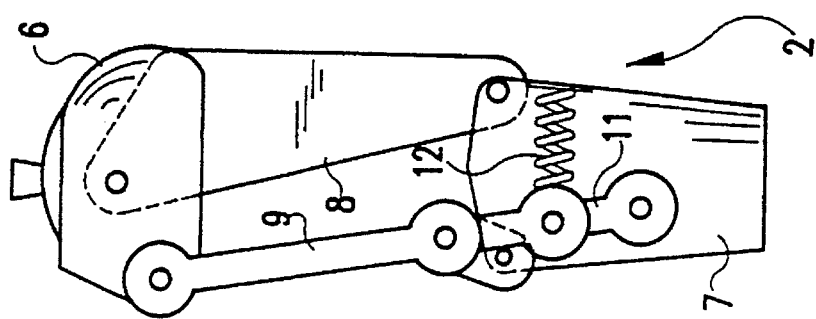

FIG. 3–5 show schematically the linkage system 2 of FIG. 2 in side view. The position depicted in FIG. 3 is the starting position. In this position the linkage system 2 is not loaded (the prosthesis 1 does not support against the leg stump) and prosthesis 1 lies in line with the leg stump (the "leg" is straight). The bottom of rear rod 9 is situated in the starting position in the highest point of the path. FIG. 4 shows the linkage system 2 in a starting position of the normal knee bending, the so-called "swing flexion". The bottom of rear rod 9 has displaced downward and to the left relative to the position of FIG. 1. This displacement takes place counter to the bias of spring means 12, whereby a force is exerted on the linkage system such that linkage system 2 will return to the starting position if no external force is exerted thereon. FIG. 5 shows the linkage system 2 at the beginning of the standing phase, that is, from the heel contact and during the standing phase, this position is the so-called stance flexion. This position provides inter alia for shock absorption and a natural walking pattern. This figure shows the beginning of the stance flexion. The bottom of rear rod 9 has displaced downward and to the right relative to the position of FIG. 3.

Figure 7:
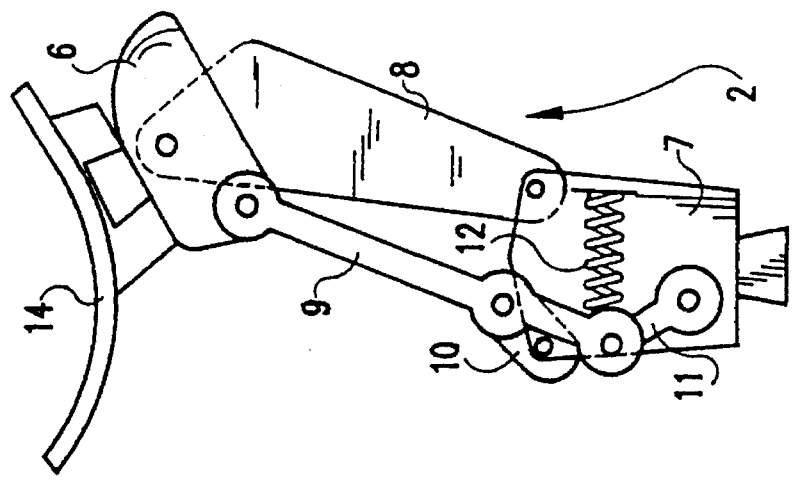
Figure 6:
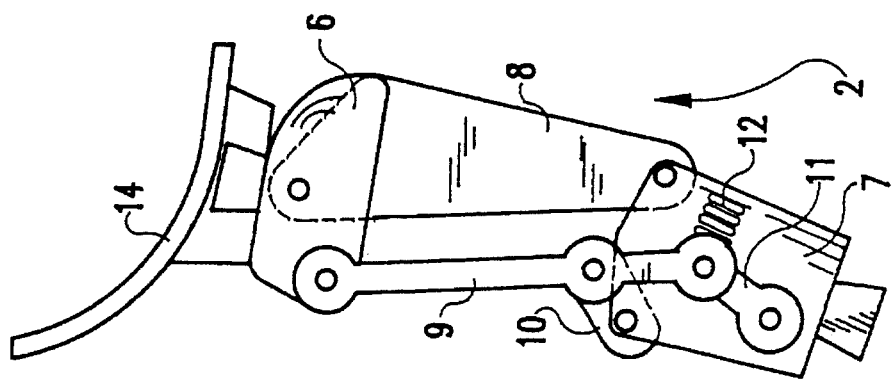
Figure 9:
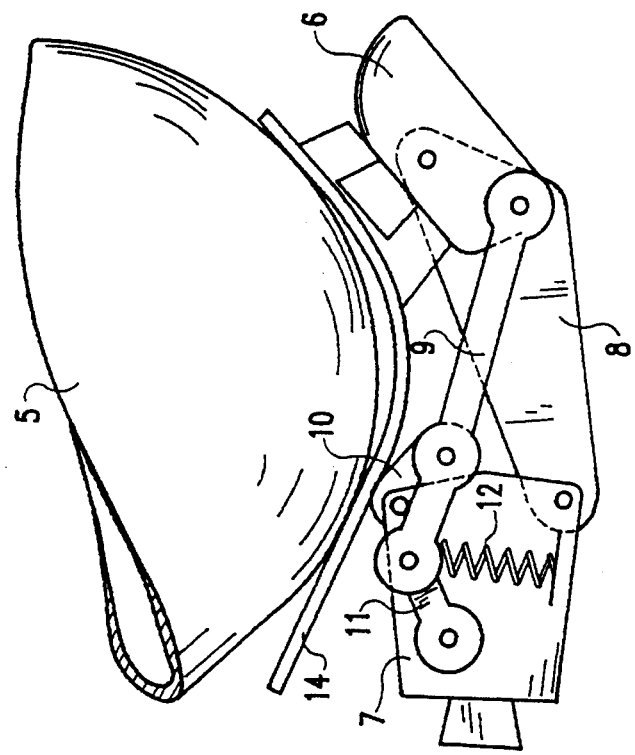
Figure 8:
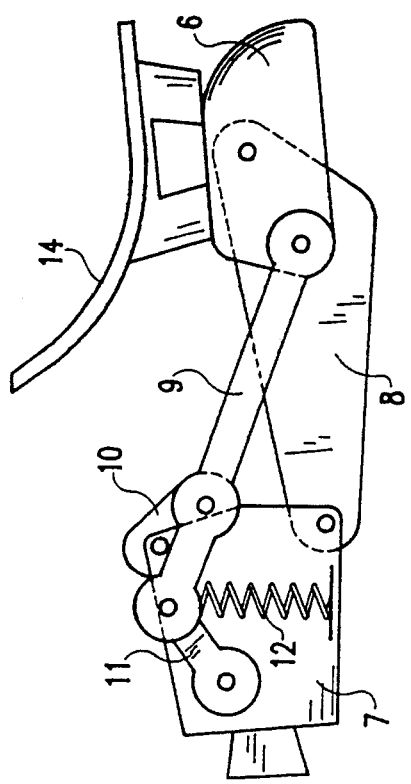

FIG. 6 shows the linkage system 2 in a stance flexion continued further than shown in FIG. 5. Further visible is a brace 14 which makes linkage system 2 particularly suitable for use by a patient with a knee exarticulation. A knee exarticulation is an amputation, literally severing in the-knee joint. FIG. 7 shows linkage system 2 with brace 14 in a swing flexion which is continued further than the swing flexion shown in FIG. 4. FIG. 8 shows the same linkage system 2 in a swing flexion continued still further than in FIG. 7. FIG. 9 shows linkage system 2 in the maximum bent position. In the far advanced swing flexion shown in FIG. 8 and 9 it can be seen clearly that the rod 8 functions as "kneecap". The linkage system 2 is embodied such that it is even possible to support on the rod 8 without the system 2 undergoing adverse effects therefrom. This is the case for instance during kneeling.

Figure 10:
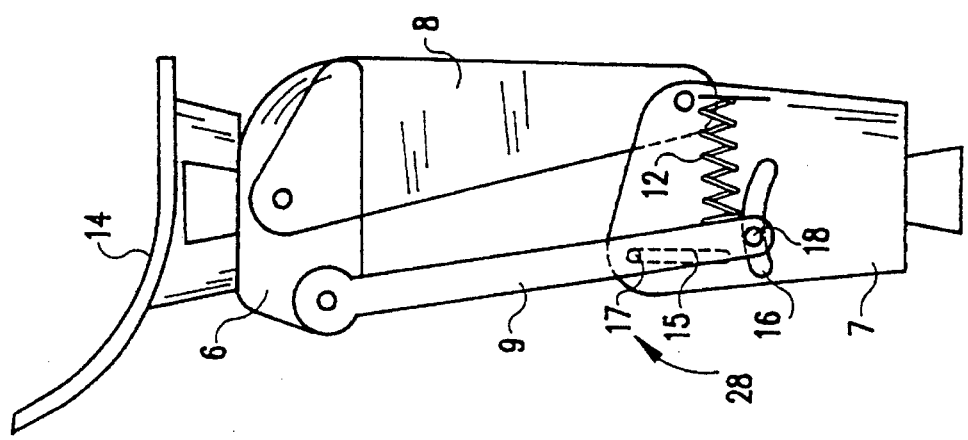
FIG. 10 shows schematically an alternative linkage system provided with two pin/slot connections.

FIG. 10 shows an alternative linkage system 28 in the starting position. The lower output rod 7 is provided with slots 15, 16 which co-act with pins 17, 18 which are fixed to the bottom of rear rod 9. During pivoting of linkage system 28 the rear rod 9 will make a constrained movement relative to the lower output rod 7 because the pins 17, 18 move in the slots 15, 16.

Figure 11:
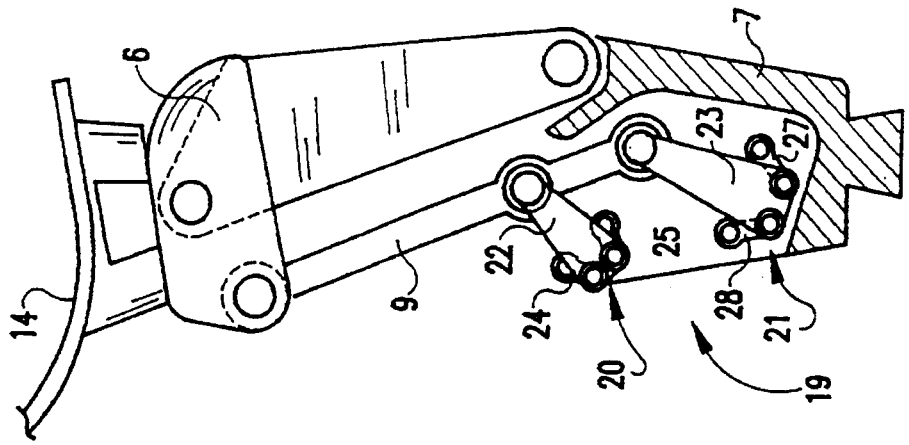
FIG. 11 shows another alternative linkage system provided with ten rods.

FIG. 11 shows another differently embodied linkage system 19 according to the invention. In this mechanism the rear rod 9 is connected with interposing of two additional three-linkage systems 20, 21 to the lower output rod 7. These three-linkage systems 20, 21 consist of a rod 22, 23 pivotally connected to the rear rod 9 and two connecting rods 24, 25, 26, 27 which are connected to the rod 22, 23 and which are also pivotally connected to the lower output rod 7. It should be apparent that it is also possible to combine steps from the linkage systems 2, 28, 19 shown in these figures. It is thus possible for instance to combine a coupling rod 10, 11 with a slot 15, 16 and pin 17, 18 or a three-linkage system 20, 21. An example of another combination consists of a linkage system 2, 28, 19 with a slot 15, 16 and pin 17, 18 in combination with a three-linkage system 20, 21.

I claim:

1. A device for connecting and mutually pivoting parts of an orthopaedic apparatus having an extension side and a flexion side opposite said extension side, said device comprising:

a kinematic multiple linkage system with at least four linkages, adjoining linkages of said at least four linkages having a common pivot axis, wherein the pivot axes extend substantially mutually parallel;

an extension side linkage of said at least four linkages located on said extension side, directly pivotally connected only to an upper output linkage of said at least four linkages and to a lower output linkage of said at least four linkages; and a flexion side linkage of said at least four linkages, located on said flexion side, pivotally connected on one side to the upper output linkage of said at least four linkages and connected on another side to the lower output linkage of said at least four linkages such that said flexion side linkage performs a constrained movement relative to the lower output linkage which comprises translation as well as rotation, said flexion side linkage being connected to said lower output linkage at two points by two means for connecting, and both said two means for connecting being pivotally connected to both said flexion side linkage and said lower output linkage.

2. A device as claimed in claim 1, wherein said two means for connecting includes at least one coupling rod, the coupling rod being pivotally connected to both the flexion side linkage and the lower output linkage.

3. A device as claimed in claim 1, wherein said two means for connecting includes two coupling rods, both coupling rods being pivotally connected to both the flexion side linkage and the lower output linkage and the rods and linkages forming a so-called Stephenson six-linkage system.

4. A device as claimed in claim 1, wherein said two means for connecting includes at least one three-linkage system, said three-linkage system comprising a system rod pivotally connected to the flexion side linkage, said system rod being pivotally connected at two positions to two connecting rods which are both pivotally connected to the lower output linkage.

5. A device as claimed in claim 4, wherein said two connecting means includes two three-linkage systems.

6. A device as claimed in claim 1, wherein said two connecting means includes at least one pin/slot connection.

7. A device as claims in claim 6, wherein said two connecting means includes two pin/slot connections.

8. A device as claimed in claim 1, wherein at least one of the at least four linkages comprises multiple sections.

9. A device as claimed in claim 1, wherein the device further comprises means, connected to at least two of the at least four linkages, for biasing said flexion side linkage in a direction relative to said lower output linkage.

10. A connection device for an orthopaedic apparatus which allows mutual pivoting, comprising:

an upper output linkage;

a lower output linkage;

an extension side linkage connecting said upper output linkage and said lower output linkage, said extension side linkage being pivotally connected to said upper output linkage at a first location on said upper output linkage and being directly pivotally connected to said lower output linkage at a first location on said lower output linkage at first and second ends of said extension side linkage, respectively;

a flexion side linkage positioned adjacent said extension side linkage; and means for connecting said flexion side linkage to both a second location on said upper output linkage and a second location on said lower output linkage, said means for connecting including:

(i) means for pivotally connecting said upper output linkage at said second location of said upper output linkage to a first portion of said flexion side linkage, said means for pivotally connecting allowing pivotal movement of said flexion side linkage relative to said upper output linkage in unison with pivotal movement of said extension side linkage relative to upper output linkage;

(ii) means for constraining movement of a second portion of said flexion side linkage relative to said lower output linkage positioned at said second location on said lower output linkage, said means for constraining movement including both a means for translational movement of said flexion side linkage relative to said lower output linkage, and a means for rotational movement of said flexion side linkage relative to said lower output linkage, said means for constraining movement comprising two means for connecting, each of said two means for connecting being pivotally connected to both said lower output linkage and said flexion side linkage.

11. A connection device as recited in claim 10 wherein said two means for connecting include at least one coupling rod pivotally connected to both said lower output linkage and said flexion side linkage.

12. A connection device as recited in claim 10 wherein said two means for connecting include two coupling rods, each of said coupling rods being pivotally connected to both said lower output linkage and said flexion side linkage.

13. A connection device as recited in claim 12 wherein at least one of said upper output linkage, said lower output linkage, said extension side linkage, said coupling rods, and said flexion side linkage is comprised of more than one element connected together.

14. A connection device as recited in claim 12 further comprising means, operatively connected to said lower output linkage and at least one of said flexion side linkage and said coupling rods, for biasing said flexion side linkage in a direction relative to said lower output linkage.

15. A connection device as recited in claim 10 wherein said two means for connecting include:

at least one three-linkage rod network comprising two connecting rods, each of said connecting rods being pivotally connected to said lower output linkage; and a system rod pivotally connected to both of said connecting rods and said flexion side linkage.

16. A connection device as recited in claim 15 wherein said two means for connecting include two three-linkage rod networks.

17. A connection device as recited in claim 10 wherein said two means for connecting include at least one pin positioned on said flexion side linkage, said pin being positioned to slide within a slot in said lower output linkage.

18. A connection device as recited in claim 10 wherein said two means for connecting include first and second pins each of which is positioned on said flexion side linkage, said first and second pins being respectively positioned to slide within first and second slots in said lower output linkage.

19. A device for connecting and mutually pivoting parts of an orthopaedic apparatus having an extension side and a flexion side opposite said extension side, said device comprising:

a kinematic multiple linkage system with at least four linkages, adjoining linkages of said at least four linkages having a common pivot axis, wherein the pivot axes extend substantially mutually parallel;

an extension side linkage of said at least four linkages, located on said extension side, directly pivotally connected only to an upper output linkage of said at least four linkages and to a lower output linkage of said at least four linkages; and a flexion side linkage of said at least four linkages, located on said flexion side, pivotally connected on one side to the upper output linkage of said at least four linkages and connected on another side to the lower output linkage of said at least four linkages such that said flexion side linkage performs a constrained movement relative to the lower output linkage which comprises translation as well as rotation, wherein said constrained movement requires said device to pivot toward said flexion side linkage, said flexion side linkage being connected with interposing of two coupling rods to the lower output linkage, both coupling rods being pivotally connected to both the flexion side linkage and the lower output linkage and the rods and linkages forming a so-called Stephenson six-linkage system.

* * * * *